United States Patent [19]

Banholzer

[11] Patent Number: 4,783,534

[45] Date of Patent: Nov. 8, 1988

[54] N-ALKYLNORSCOPINES AND ACID ADDITION SALTS THEREOF

[75] Inventor: Rolf Banholzer, Ingelheim am Rhein, Fed. Rep. of Germany

[73] Assignee: Boehringer Ingelheim KG, Ingelheim am Rhein, Fed. Rep. of Germany

[21] Appl. No.: 32,762

[22] Filed: Mar. 31, 1987

Related U.S. Application Data

[63] Continuation of Ser. No. 872,123, Jun. 9, 1986, abandoned, which is a continuation of Ser. No. 626,692, Jul. 2, 1984, abandoned, which is a continuation-in-part of Ser. No. 485,161, Apr. 15, 1983, abandoned.

[30] Foreign Application Priority Data

Apr. 26, 1982 [DE] Fed. Rep. of Germany ....... 3215493

[51] Int. Cl.$^4$ ............................................. C07D 451/06
[52] U.S. Cl. ................................................... 546/91
[58] Field of Search ........................................ 546/91

[56] References Cited

U.S. PATENT DOCUMENTS 4,608,377  8/1986  Banholzer et al. ................ 514/291

OTHER PUBLICATIONS

Werner et al., Chem. Abstracts, vol. 67, (9), Abst. No. 43,974w, Aug. 28, 1967.
Banholzer et al., vol. 87, (17), Abst. No. 136,106t, Oct. 24, 1977.

*Primary Examiner*—Alan L. Rotman
*Attorney, Agent, or Firm*—Weissenberger, Hammond & Littell

[57] ABSTRACT

The invention relates to novel N-alkylnorscopines wherein the alkyl group may have 2 to 10 carbon atoms, which are useful in the preparation of valuable pharmaceutical compositions. These compounds may be prepared from the corresponding N-alkylnorscopolamines by hydrogenolysis with complex hydrides, which reaction is preferably carried out with sodium borohydride in ethanol at ambient temperature.

5 Claims, No Drawings

N-ALKYLNORSCOPINES AND ACID ADDITION SALTS THEREOF

CROSS-REFERENCE TO RELATED APPLICATION

This is a continuation of copending application Ser. No. 872,123, filed June 9, 1986, now abandoned; which in turn is a continuation of Ser. No. 626,692, filed July 2, 1984, now abandoned; which in turn is a continuation-in-part of Ser. No. 485,161, filed Apr. 15, 1983, now abandoned.

FIELD OF THE INVENTION

The invention herein relates to novel N-alkylnorscopines of the formula

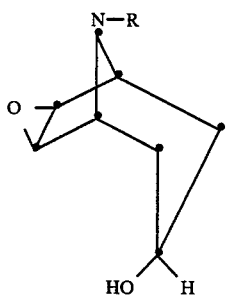
(I)

wherein R represents a linear or branched alkyl having from 2 to 10 carbon atoms, and acid addition salts thereof. The invention also relates to a process of preparation and to the further processing thereof to form pharmaceutical compositions.

The compounds of Formula I constitute valuable products which are useful, for example, in the preparation of esters such an N-alkylnorscopolamines or ethers such as 6,11-dihydro-dibenzo[b,e]-thiepine-11-N-alkylnorscopine ethers of the formula

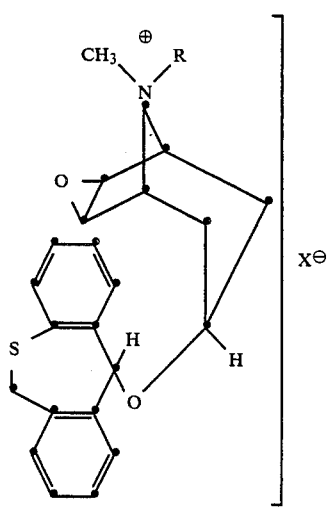
(II)

wherein R represents a linear or branched alkyl having from 2 to 10 carbon atoms and $X^{(-)}$ represents a nontoxic, pharmacologically acceptable anion such as, for example, a halogen or an organic sulfonic acid group. These substances of Formula II are, in turn, valuable pharmaceuticals with a well balanced ration of anticholinergic and antihistaminic activities, and they are, therefore, particularly suitable for the treatment of spasm and obstructive diseases of the respiratory tract. These substances are described in co-pending U.S. patent application Ser. No. 471,353, filed Mar. 2, 1983, incorporated herein by reference.

The compounds of Formula I may be further processed to form the N-alkylnorscopine ethers of Formula II by reaction with compounds of the formula

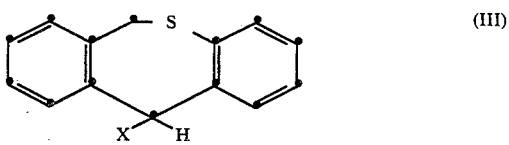
(III)

wherein X represents an easily removable group, for example, a halogen or an organic sulfonic acid group, to form tertiary compounds of the formula

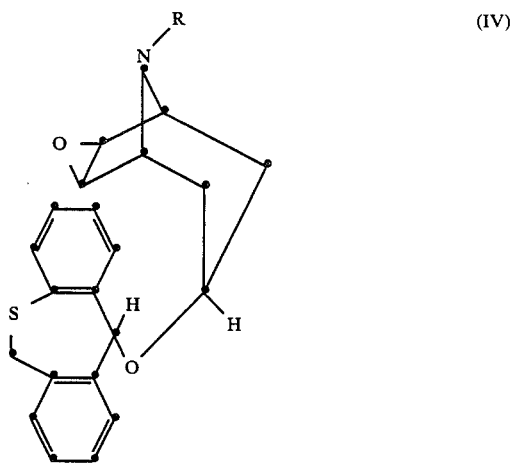
(IV)

wherein R is as defined above. The compounds of Formula IV are in turn converted into the quaternary salts of Formula II by treatment with conventional quaternization agents of the formula

$$R-X \qquad (V)$$

wherein R and X are as defined above. For further details regarding the processing of the N-alkylnorscopines of Formula I, reference may be made to U.S. patent application Ser. No. 471,353, mentioned above.

The compounds of Formula I are prepared by treating N-alkylnorscopolamines of the formula

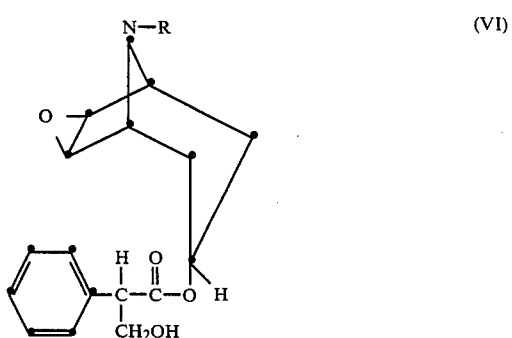
(VI)

or salts thereof, wherein R is as defined above, with suitable complex metal hydrides, preferably at ambient temperature or at lower temperatures, in a solvent. Metal borohydrides, preferably sodium borohydride (NaBH$_4$), are particularly suitable. Lithium alanate is also theoretically suitable; however, temperatures of 0° C. and below should then be used to avoid side reactions.

A particularly suitable solvent for the reaction described above is ethanol. Higher alcohols and other organic solvents, for example, ethers, are less favorable since the N-alkylnorscopolamine salts of Formula VI preferably used as starting products do not readily dissolve therein. Methanol is not particularly suitable either since it decomposes sodium borohydride, for example, very rapidly, even at 0° C., thereby requiring the use of an unnecessarily large quantity of this reagent. Hydrogenolysis of the compounds of Formula VI may also be effected in water if, for example, the pH is maintained at about 6 to 7. However, it is more difficult to isolate the N-alkylnorscopines afterwards from water than from ethanol.

The preparation of the N-alkylnorscopolamines of Formula VI is described in German published patent application (DE-AS) No. 16 70 048, incorporated herein by reference.

The compounds of Formula I may also be obtained in the form of acid addition salts after reaction with inorganic or organic acids. Suitable acids include, for example, hydrochloric, hydrobromic, sulfuric, methylsulfuric, phosphoric, tartaric, fumaric, citric, maleic, succinic, gluconic, malic, p-toluenesulfonic, methanesulfonic, and amidosulfonic acid.

N-alkylnorscopine can be converted to an ester such as an N-alkylnorscopolamine by, for example, acylation or transesterification. The details for such a procedure are set forth in, for example, U.S. Pat. No. 3,503,996, incorporated herein by reference.

The following examples are intended to illustrate the invention and should not be construed as limiting it thereto.

EXAMPLES

Example 1

N-Isopropylnorscopine and the hydrochloride thereof

A quantity of 36.8 gm (0.1 mol) of N-isopropylnorscopolamine hydrochloride is suspended in 370 ml of ethanol, and the resulting suspension is combined with 3.78 gm (0.1 mol) of sodium borohydride in six batches at intervals of 15 minutes, under constant stirring, at a temperature of 20° C. The resulting mixture is left to react for 12 hours. After this time, hydrogenolysis is complete. Then, hydrogen chloride gas is introduced under a nitrogen atmosphere, at −5° to −10° C., until an acid reaction is obtained, after which the solution is washed with 1.5 liters of ether to eliminate hydrogen chloride. After drying, finely triturated crystals are suspended in 2 liters of methylene chloride, the resulting suspension is heated to boiling, and ammonia is introduced into the boiling methylene chloride to form the base, until the reaction is complete. After the inorganic salts have been separated, the methylene chloride is distilled off under reduced pressure at 30° C.

Colorless crystals (cyclohexane),
M.p.: 118°–119.5° C.,
Yield: 15.8 gm (86.2% of theory).

The hydrochloride may be prepared by conventional methods. Colorless crystals (ethanol), melting point: 255° C. (decomposition), conversion point: ∼230° C.

The presence of this compound is confirmed by elementary analysis and spectra.

Example 2

N-Ethylnorscopine hydrochloride

An amount of 35.4 gm (0.1 mol) of N-ethylnorscopolamine hydrochloride is suspended in 350 ml of ethanol, and the resulting suspension is combined with 3.78 gm (0.1 mol) of sodium borohydride in six batches at intervals of 20 minutes, under constant stirring, at a temperature of 20° C. The remainder of the synthesis proceeds as described in Example 1. Colorless crystals (ethanol/ether) with a melting point of 139°–141° C. (decomposition) are obtained from ethanolic solution by supersaturation with ether.

Example 3

N-n-propylnorscopine hydrochloride

The above compound is prepared from 36.8 gm (0.1 mol) of N-n-propylnorscopolamine by use of 3.78 gm (0.1 mol) of sodium borohydride in ethanol in accordance with the procedure described in Example 1.

Colorless crystals (from ethanol/ether), melting point: 241°–241.5° C. (decomposition).

Example 4

N-n-Butylnorscopine hydrochloride

The above compound is prepared from 38.2 gm (0.1 mol) of N-n-butylnorscopolamine by use of 3.78 gm (0.1 mol) of sodium borohydride in ethanol in accordance with the procedure described in Example 1.

Colorless crystals (from acetonitrile), melting point: 198° C.

Example 5

The following compounds corresponding to the compounds of the instant application and the prior art were tested for spasmolysis:

Prior Art

A=scopine tropic ester (Scopolamine), prepared by isolation from Datura metel L.; standardized alkaloid.

Corresponding To The Invention

B=N-ethylnorscopine tropic acid ester (N-ethylnorscopolamine), prepared by transesterification method according to U.S. Pat. No. 3,583,996 (analogously to Example 1) from N-ethylnorscopine.

C=N-isopropylnorscopine tropic acid ester (N-isopropylnorscopolamine), prepared by transesterification method according to U.S. Pat. No. 3,583,996 (analogously to Example 1) from N-isopropylnorscopine.

TESTING PROTOCOL

The testing was carried out on the isolated guinea pig ileum using the method described by R. MAGNUS, Pflügers Arch. 102, 123 (1904). A section of ileum about 2 cm long taken from a guinea pig which had been killed by a blow on the back of the neck was suspended in a organ bath with Lock-Ringer's solution. The temperature of the organ bath was 35° C. The contractions in the longitudinal muscle caused by a spasmogen (acetylcholine or histamine) were recorded on a kymograph. The spasmolytic agent or control substance (e.g., atropine or diphenhydramine) was added to the organ bath 90 seconds before the spasmogen was administered (preventive method). Both the control substance and the spasmolytic agent to be tested were metered in increasing concentrations so that the activity of the spasmogen was inhibited by from about 10 to 90%.

The testing was carried out using a self-made spasmolysis apparatus. Only those preparations for which it was possible to draw up a dosage activity curve both for the control substance and for the spasmolytic substance being tested, on the same section of intestine, were evaluated.

RESULTS

The testing results are set forth in the following table:

TABLE

| COMPOUND | Spasmolysis (Atropine = 1) |
|---|---|
| A* | 1.09 |
| B | 1.8 |
| C | 4.9 |

*Prior Art

It can be readily seen that compounds prepared from compounds according to the invention are significantly more effective than a compound prepared from a prior art compound.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A compound of the formula

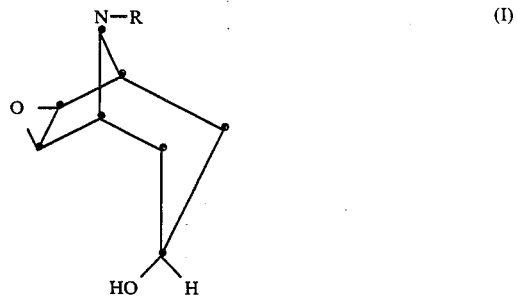

wherein R represents a linear or branched alkyl having from 2 to 10 carbon atoms, or an acid addition salt thereof.

2. The compound of claim 1 which is N-isopropylnorscopine or an acid addition salt thereof.

3. The compound of claim 1 which is N-ethylnorscopine or an acid addition salt thereof.

4. The compound of claim 1 which is N-n-propylnorscopine or an acid addition salt thereof.

5. The compound of claim 1 which is N-n-butylnorscopine or an acid addition salt thereof.

* * * * *